(12) United States Patent
Jin et al.

(10) Patent No.: US 8,507,691 B2
(45) Date of Patent: Aug. 13, 2013

(54) PROCESS FOR CONTINUOUSLY PRODUCING 3-ISOTHIAZOLINONE DERIVATIVES AND INTERMEDIATE PRODUCTS THEREOF

(75) Inventors: Yuechun Jin, Beijing (CN); Kezhong Li, Beijing (CN); Xueting Lu, Beijing (CN); Xiaolin Zhang, Beijing (CN); Yu Wang, Beijing (CN); Shuailin Zhou, Beijing (CN); Chao Li, Beijing (CN)

(73) Assignee: Beijing Tianqing Chemicals Co. Ltd., Beijing (CN)

( * ) Notice: Subject to any disclaimer, the term of this patent is extended or adjusted under 35 U.S.C. 154(b) by 164 days.

(21) Appl. No.: 12/738,902

(22) PCT Filed: Oct. 24, 2008

(86) PCT No.: PCT/CN2008/072831
§ 371 (c)(1),
(2), (4) Date: Apr. 20, 2010

(87) PCT Pub. No.: WO2009/056069
PCT Pub. Date: May 7, 2009

(65) Prior Publication Data
US 2010/0234613 A1 Sep. 16, 2010

(30) Foreign Application Priority Data
Oct. 25, 2007 (CN) .......................... 2007 1 0163464

(51) Int. Cl.
*C07D 275/03* (2006.01)
(52) U.S. Cl.
USPC ........................................................ 548/213
(58) Field of Classification Search
USPC ........................................................ 548/213
See application file for complete search history.

(56) References Cited

U.S. PATENT DOCUMENTS

| | | | |
|---|---|---|---|
| 3,769,315 A * | 10/1973 | Keener et al. ................. | 558/387 |
| 4,052,440 A * | 10/1977 | Gladstone et al. ............ | 560/154 |
| 5,315,008 A | 5/1994 | Effenberger et al. | |
| 2008/0227986 A1* | 9/2008 | Jin ................................ | 548/213 |

FOREIGN PATENT DOCUMENTS

| CN | 101050203 A | | 10/2007 |
|---|---|---|---|
| JP | 2003335763 A | * | 11/2003 |
| WO | WO 2007112613 A1 | * | 10/2007 |

OTHER PUBLICATIONS

Machine translation of JP 2003335763 A by Koshiyama, obtained from http://dossier1.ipdl.inpit.go.jp/AIPN/odse_top_fwi.ipdl?N0000=7401 on Jun. 26, 2012.*
Merriam-Webster Entry for "aqueous", obtained from http://www.merriam-webster.com/dictionary/aqueous on Jan. 9, 2013.*
Dongming, S., et al., "Study on the Synthesis of 5-Chloro-2-Methyl-lsothiazolone-3," *Fine Petrochemical Industry*, No. 4, pp. 52-55 (1995).
Miller, G., et al., "Isothiazoles II: 5-Chloro-4-isothiazolin-3-ones," *Journal of Heterocyclic Chemistry*, vol. 8, pp. 581-586 (1971).
Mueller, W., "The Base-Catalyzed Reaction of Hydrogen Sulfide with α-Chloromethyl Acrylate and α-Chloroacrylonitrile," The Journal of Organic Chemistry, vol. 34(10), pp. 2955-2957 (Oct. 1969).

* cited by examiner

*Primary Examiner* — Joseph Kosack
*Assistant Examiner* — Matthew Coughlin
(74) *Attorney, Agent, or Firm* — Kilpatrick, Townsend & Crew LLP (57) ABSTRACT

The present application provides a process for continuously producing 3-isothiazolinone derivatives and intermediate products thereof, comprising continuously carrying out four steps, i.e., sulfuration, purification, amination and chlorination. Compared with the batch process of the prior art, the process of the present application may reduce the amount of manufacturing devices, lower energy consumption, simplify operations, and is therefore particularly suitable for mass production.

15 Claims, 4 Drawing Sheets

PROCESS FOR CONTINUOUSLY PRODUCING 3-ISOTHIAZOLINONE DERIVATIVES AND INTERMEDIATE PRODUCTS THEREOF

RELATED APPLICATIONS

The present application is a U.S National Stage Application of PCT/CN2008/072831, filed Oct. 24, 2008, which claims all benefits of the Chinese application No. 200710163464.4, filed on Oct. 25, 2007, entitled "a process for continuously producing 3-isothiazolinone derivatives", the contents of which are explicitly incorporated herein by reference in their entirety.

TECHNICAL FIELD

The present application is directed to a process for producing 3-isothiazolinone derivatives. More particularly, the present application is directed to a process for continuously producing 3-isothiazolinone derivatives and intermediate products thereof.

DESCRIPTION OF RELATED ARTS

Isothiazolinone compounds belong to a class of novel broad-spectrum bactericide, which have high efficiency, broad spectrum, low toxicity, innocuity under using concentration, natural degradation in the environment, and the like. Therefore, isothiazolinone compounds are widely used in the fields of industrial water treatment, paper making, cosmetics, construction materials, bonding adhesive, paints, medical treatment and public health, textiles, photography, detergents, and the like. In particular, 2-alkyl-4,5-disubstituted-4-isothiazolin-3-ones are better bactericides and preservatives.

The production of 3-isothiazolinone derivatives generally comprises four steps, i.e. sulfuration, purification, amination and chlorination. The corresponding reaction equations are as follows:

1. $CH_2=CHCO_2CH_3 + H_2S + S \longrightarrow$
$(SCH_2CH_2CO_2CH_3)_2 + S(SCH_2CH_2CO_2CH_3)_2$
  I                                II                              III
2. $S(SCH_2CH_2CO_2CH_3)_2 + Na_2SO_3 \longrightarrow (SCH_2CH_2CO_2CH_3)_2 +$
  III                                                                    II
  $Na_2S_2O_3$
3. $(SCH_2CH_2CO_2CH_3)_2 + NH_2R \longrightarrow (SCH_2CH_2CONHR)_2 +$
  II                       IV                                V
  $CH_3OH$
4. $(SCH_2CH_2CONHR)_2 + Cl_2 \longrightarrow IT\text{-}HCl + HCl$ wherein
  V                                                     VI

IT =

In the prior art, all of the above four steps are carried out in a batch process, which is easy and convenient for small production. However, the problems such as more apparatus for batch process, large quantity of online raw materials and intermediates, long period for reaction, high energy consumption and small safety coefficient show up as the production increases.

SUMMARY

In order to make an improvement to the prior art, the present application provides a process for producing 3-isothiazolinone derivatives. In the process, all the steps of sulfuration, purification, amidation and chlorination in the production of 3-isothiazolinone derivatives are carried out in a continuous process, and all the steps as a whole may be combined together to form a continuous production process, thereby reducing production apparatus, lowering the energy consumption, simplifying operations and enhancing production safety.

In one aspect, the present application is directed to a process for preparing a compound of formula II, comprising continuously adding a compound of formula I, sulfur and $H_2S$ to a first reaction device to carry out the following reaction, $CH_2=CHCO_2CH_3 + H_2S + S \longrightarrow$
I
$(SCH_2CH_2CO_2CH_3)_2 + S(SCH_2CH_2CO_2CH_3)_2.$
II                              III In a preferred embodiment, the process comprises:
i) continuously adding the compound of formula I, sulfur and $H_2S$ to a first reaction device; and
ii) filtering the reaction solution overflowing the first reaction device to obtain a solid and a two-phase filtrate, wherein the solid and water phase are returned to the first reaction device.

In another aspect, the present application is directed to a process for refining a mixture comprising a compound of formula II and a compound of formula III, comprising continuously adding the mixture and an aqueous solution of sodium sulfite to a second reaction device to carry out the following reaction, $S(SCH_2CH_2CO_2CH_3)_2 + Na_2SO_3 \longrightarrow$
III
$(SCH_2CH_2CO_2CH_3)_2 + Na_2S_2O_3.$
II In a preferred embodiment, the process comprises:
1) continuously adding the mixture and an aqueous solution of sodium sulfite to a first counter-current extraction column; and
2) continuously adding the organic layer obtained from step 1) and water to a second counter-current extraction column to obtain a compound of formula II.

In yet another aspect, the present application is directed to a process for preparing a compound of formula V, comprising continuously adding a compound of formula II and a primary amine of formula IV to a third reaction device to carry out the following reaction, $(SCH_2CH_2CO_2CH_3)_2 + NH_2R \longrightarrow$
II                       IV

$(SCH_2CH_2CONHR)_2 + CH_3OH$

V wherein R represents $C_1$-$C_{18}$ alkyl or $C_3$-$C_{18}$ cycloalkyl.

In a preferred embodiment, the process comprises:
a) continuously adding the compound of formula II and the primary amine of formula IV to a third reaction device to react; and
b) subjecting the products obtained form step a) to a solid-liquid separation to obtain a solid and a mother liquid, wherein the mother liquid is returned to the third reaction device.

In yet another aspect, the present application is directed to a process for preparing a compound of formula VI, comprising continuously adding a compound of formula V and chlorine to a fourth reaction device to carry out the following reaction, wherein IT =

R represents $C_1$-$C_{18}$ alkyl or $C_3$-$C_{18}$ cycloalkyl, and $R_1$ and $R_2$ independently represent H or chlorine.

In a preferred embodiment, the process comprises:
A) continuously adding the compound of formula V and chlorine to a fourth reaction device; and
B) subjecting the reaction solution overflowing the fourth reaction device to a solid-liquid separation to obtain a solid and a mother liquid.

In other aspects, the present application is directed to a process for producing 3-isothiazolinone derivatives, comprising continuously carrying out the following four steps:
(1) continuously adding a compound of formula I, sulfur and $H_2S$ to a first reaction device to obtain a first reaction solution comprising a compound of formula II and a compound of formula III;
(2) continuously adding the first reaction solution and an aqueous solution of sodium sulfite to a second reaction device to obtain a second reaction solution comprising a compound of formula II;
(3) continuously adding the second reaction solution and a primary amine of formula IV to a third reaction device to obtain a compound of formula V; and
(4) continuously adding the compound of formula V and chlorine to a fourth reaction device to obtain a compound of formula VI.

In yet another aspect, the present application is directed to a process for producing 3-isothiazolinone derivatives, comprising two or more optional combinations of a process in each step aforementioned.

In yet another aspect, the present application is directed to a product obtained from any one of the aforementioned processes.

By employing the continuous process of the present application for producing 3-isothiazolinone derivatives, it is possible to reduce the amount of manufacturing apparatus, lower energy consumption, simplify operations, and enhance safety of the production.

DETAILED DESCRIPTION

In the following description, certain specific details are included to provide a thorough understanding of various disclosed embodiments. One skilled in the relevant art, however, will recognize that embodiments may be practiced without one or more of these specific details, or with other processes, components, materials, and the like.

Unless the context requires otherwise, throughout the specification and claims which follow, the word "comprise" and variations thereof, such as, "comprises" and "comprising" are to be construed in an open, inclusive sense, which is as "including, but not limited to".

Reference throughout this specification to "one embodiment", or "an embodiment", or "in another embodiment", or "some embodiments", or "in some embodiments" means that a particularly referred feature, structure, or characteristic described in connection with the embodiment is included in at least one embodiment. Thus, the appearance of the phrases "in one embodiment", or "in an embodiment", or "in another embodiment", or "in some embodiments" in various places throughout this specification are not necessarily all referring to the same embodiment. Furthermore, the particular features, structures, or characteristics may be combined in any suitable manner in one or more embodiments.

It should be noted that, as used in this specification and the appended claims, the singular forms "a", "an", and "the" include plural referents unless the content clearly dictates otherwise. Thus, for example, reference to a solvent containing "a substance having polyhydroxy and/or polyamino groups" includes a single substance having polyhydroxy and/or polyamino groups, or two or more substances having polyhydroxy and/or polyamino groups. It should also be noted that the term "or" is generally employed in its sense including "and/or" unless the content clearly dictates otherwise.

Definition

Certain chemical groups named herein are preceded by a shorthand notation indicating the total number of carbon atoms that are to be found in the indicated chemical group. For example, $C_7$-$C_{12}$ alkyl describes an alkyl group, as defined below, having a total of 7 to 12 carbon atoms, and $C_4$-$C_{12}$ cycloalkylalkyl describes a cycloalkylalkyl group, as defined below, having a total of 4 to 12 carbon atoms. The total number of carbons in the shorthand notation does not include carbons that may exist in substituents of the group described.

As used herein, "$C_m$ to $C_n$" or "$C_{m\ to\ n}$" in which "m" and "n" are integers refers to the number of carbon atoms in an alkyl, or the number of carbon atoms in the ring of a cycloalkyl group. That is, the alkyl or ring of the cycloalkyl can contain from "m" to "n", carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "m" and "n" are designated with regard to an alkyl or cycloalkyl group, the broadest range described in these definitions is to be assumed.

Accordingly, as used in the specification and appended claims, unless specified to the contrary, the following terms have the meaning indicated:

The term "alkyl" as used herein means any unbranched or branched, substituted or unsubstituted, saturated hydrocarbon. The alkyl moiety may be branched, straight chain, or cyclic. The alkyl group may have 1 to 18 carbon atoms (whenever it appears herein, e.g., a numerical range such as "1 to 18" refers to each integer in the given range; e.g., "1 to 18 carbon atoms" means that the alkyl group may consist of 1 carbon atom, 2 carbon atoms, 3 carbon atoms, and the like, up to and including 18 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is(are) one or more group(s) individually and independently selected from substituted or unsubstituted cycloalkyl, substituted or unsubstituted alkoxy, alkylthio, halo, carbonyl, keto, nitro, silyl, trihalomethanesulfonyl, and amino groups including disubstituted amino groups. Typical alkyl groups include, but are in no way limited to, methyl, ethyl, propyl, iso-propyl, butyl, iso-butyl, t-butyl, pentyl, hexyl, cyclopropyl, cyclobutyl, cyclopentyl, cyclohexyl, and the like. Wherever a substituent is described as being "optionally substituted", that substitutent may be substituted with one of the above substituents.

The term "cycloalkyl" as used herein alone or as part of a group refers to a completely saturated (no double bonds) mono- or multi-cyclic hydrocarbon ring system. When composed of two or more rings, the rings may be joined together in a bridged or spiro-connected fashion. Cycloalkyl groups of this application may range from $C_3$ to $C_{18}$. In some embodiments, it may range from $C_3$ to $C_{10}$. In some embodiments, it may range from $C_3$ to $C_6$. A cycloalkyl group may be substituted or unsubstituted. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated.

The term "halo" or "halogen" refers to bromo, chloro, fluoro or iodo.

The term "optional" or "optionally" means that the subsequently described event of circumstances may or may not occur, and that the specification includes instances where said event or circumstance occurs and instances in which it does not.

Unless stated otherwise, when one substituent is regarded as "optionally substituted", it means that the substituent may be individually and independently substituted by one or more substituents selected from the group consisting of cycloalkyl, alkylthio, arylthio, halo, carbonyl, silyl, trihalomethanesulfonyl and amino groups including disubstituted amino groups.

For example, "optionally substituted aryl" means that said aryl may be substituted or may not be substituted, and the Specification includes substituted aryl groups and aryl groups without substituents.

As used herein, the term "reaction device" may refer to a single reaction device or a reaction device system composed of several reaction devices connected in series or in parallel.

As used herein, the term "reactor" refers to a device suitable for carrying out a chemical reaction, which includes, but is not limited to, kettle, pot, tank, column and the like.

"$H_2S$, primary amine, chlorine" used in the present application may be gaseous or liquid.

In the art of the present application, a batch process, also referred to as an intermittent process, refers to that all the steps are carried out at the same location but at different times. The operation conditions of the process are unstable, and the parameters of the process vary over time. For example, a batch of materials is added into a device. The products are discharged in batch after operation. The device is cleaned. New materials are added into the device again. Such a process is repeated.

A continuous process in the art refers to that all the steps are carried out at different locations but at the same time. The operation conditions are stable and the raw materials are fed and the final products are yielded continuously. During the operation, various parameters of the materials at any location actually remain constant. It is easy for a continuous process to achieve mechanization and automation. The products from the process have uniform quality and the devices for the process are compact. The process also has the advantages of larger production capacity, less intensity of work and the like.

A semi-continuous process in the art is a combination of a continuous process and a batch process. In other words, in the whole production process, some steps are carried out in a continuous process while other steps are carried out in a batch process. For example, in a solid-liquid separation settler, the liquid mixture to be separated, which is a thin suspension, is continuously fed. The supernatant liquids continuously overflow the top of the settler while the precipitates settled on the bottom are discharged after being accumulated to a certain amount. This process is a semi-continuous process.

In series (reaction devices connected in series) generally mean that the materials leaving the previous reaction device is the feed of the next reaction device. The materials are continuously added to the first reaction device, flow successively through each reaction device, and are discharged from the last reaction device.

In parallel (reaction devices connected in parallel) generally mean that the inlet pipes of all the reaction devices are combined together and the outlet pipes are also combined together, i.e., reaction devices are connected in such a way that the reaction devices separate from one point and converge at another point.

Reaction Scheme

As described previously, the production of 3-isothiazolinone derivatives generally comprises four steps, i.e., sulfuration, purification, amination and chlorination, all of which are carried out in a batch process in the prior art. To overcome a defect of the prior art and establish a modified process for producing 3-isothiazolinone derivatives, the present inventors conducted an in-depth research on the above mentioned four-step reaction process.

Reaction Process of Sulfuration:

To a reaction kettle was added an aqueous solution of ammonium sulfide and sulfur powder. The resultant mixture was cooled. A compound of formula I was then added dropwise with stirring meanwhile $H_2S$ was introduced. The raw materials were added over several hours. The resultant mixture was stood to separate so as to give a liquid mixture of a compound of formula II and a compound of formula III. Through monitoring the reaction via chromatography analysis, it was found that the reaction completes within several minutes to generate a compound of formula II and a compound of formula III after a compound of formula I was added into the reaction kettle. The time was mainly spent on feeding, cooling and separating.

Reaction Process of Purification:

Into a reaction kettle was added a liquid mixture of a compound of formula II and a compound of formula III and a suitable amount of an aqueous solution of sodium sulfite. The resultant mixture was heated and stirred for several hours. The organic layer was washed with water. The mixture was separated to give a refined compound of formula II. Through monitoring the reaction via chromatography analysis, it was found that the compound of formula III was transformed to the compound of formula II within tens of minutes under the controlled temperature range. Therefore, it was not necessary to complete the reaction over several hours.

Reaction Process of Amidation:

wherein R represents $C_1$-$C_{18}$ alkyl or $C_3$-$C_{18}$ cycloalkyl.

A reaction kettle was cooled. To the reaction kettle were added a refined compound of formula II and a solution of a primary amine of formula IV in alcohol. The resultant mixture was stirred for tens of hours and separated to give a compound of formula V with purity of more than 98%. Through monitoring the reaction via chromatography analysis, it was found that the generation speed of a compound of formula V was fastest in the first 10 hours of the reaction and was nearly constant, and then gradually decreased. The amount of an intermediate reaches the maximum after 5 hours of reaction. The compound of formula II was consumed by about 85% within the first 10 hours of reaction. The rest time were only spent by the remaining 15% of the compound of formula II on transforming to the intermediate and by about 37% of the generated intermediate on transforming to a compound of formula V (see Table 1).

TABLE 1

Variation of Contents of Materials Over Time During Reaction Process

| reaction time (hrs) | Compound of formula II | Intermediate | Compound of formula V |
|---|---|---|---|
| 5 | 28 | 49 | 23 |
| 10 | 15 | 37 | 48 |
| 15 | 9 | 32 | 59 |
| 20 | 7 | 27 | 66 |
| 25 | 4 | 22 | 74 |

Contents of tested materials(%)

Reaction Process of Chlorination:

wherein IT =

R represents $C_1$-$C_{18}$ alkyl or $C_3$-$C_{18}$ cycloalkyl, and $R_1$ and $R_2$ independently represent H or chlorine.

Into a reaction device was added ethyl acetate. Ethyl acetate was cooled. A compound of formula V and chlorine were added at the same time in batch with stirring (for example, R=$CH_3$) within several hours. A solid-liquid separation of the mixture was carried out to give a compound of formula VI (for example, R=$CH_3$, R1=H, R2=H or Cl) as a solid. Through monitoring the reaction via chromatography analysis, it was found that the reaction was completed within several minutes after a compound of formula V was added into the reaction device. Like the reaction of sulfuration, feeding and cooling occupied the most of the time.

Based on the above results and a large number of experiments, the inventors eventually completed the continuous process for producing 3-isothiazolinone derivatives of the present application.

Embodiments

In one aspect, the present application is directed to a process for preparing a compound of formula II, comprising continuously adding a compound of formula I, sulfur and $H_2S$ to a first reaction device to carry out the following reaction, In some embodiments, the reaction for preparing a compound of formula II is carried out in an aqueous solution of ammonium sulfide.

In some preferred embodiments, a process for preparing a compound of formula II comprises:
i) continuously adding a compound of formula I, sulfur and $H_2S$ to a first reaction device; and
ii) filtering the reaction solution overflowing the first reaction device to obtain a solid and a two-phase filtrate, wherein the solid and water phase are returned to the first reaction device.

In some preferred embodiments, a process for preparing a compound of formula II comprises:
i) continuously adding a compound of formula I, sulfur and H₂S to a first reaction device in an aqueous solution of ammonium sulfide; and
ii) filtering the reaction solution overflowing the first reaction device to obtain a solid and a two-phase filtrate, wherein the solid and water phase return to the first reaction device.

In some more preferred embodiments, a process for preparing a compound of formula II comprises:
i) continuously adding a compound of formula I, an aqueous solution of ammonium sulfide, sulfur and H₂S to the first reaction device;
ii) filtering the reaction solution overflowing the upper part of the first reaction device to obtain a solid and a two-phase filtrate, wherein the solid and water phase are returned to the first reaction device; and
iii) gravitationally separating the filtrate obtained from step ii) to obtain an upper layer liquid comprising ammonium sulfide and a lower layer liquid comprising a compound of formula II and a compound of formula III, wherein the upper layer liquid is returned to the first reaction device.

In some embodiments, the concentration of an aqueous solution of ammonium sulfide is about 5-20%.

In some embodiments, H₂S used to prepare a compound of formula II may be gaseous or liquid.

In some embodiments, the first reaction device comprises several reactors.

In some preferred embodiments, the first reaction device comprises 1 to 10 reaction kettles.

In some more preferred embodiments, several reaction kettles may be connected in series or in parallel or partly in parallel.

In some preferred embodiments, the first reaction device comprises 1 to 4 continuous reaction towers or extraction columns.

In some embodiments, the compound of formula I, ammonium sulfide solution, sulfur and H₂S are fed into the reaction device in a total rate of 1 g to 100 kg per minute.

In some embodiments, the mass ratio of the compound of formula I, ammonium sulfide, sulfur and H₂S is about 1:0.01-0.25:0.2-0.5:0.2-0.3.

In some preferred embodiments, the mass ratio of the compound of formula I, ammonium sulfide, sulfur and H₂S is about 1:0.065:0.26:0.22.

In some embodiments, the reaction for preparing a compound of formula II is carried out at about 15-25° C.

In some embodiments, the reaction for preparing a compound of formula II is carried out for about 5-15 hours.

Figure 1:
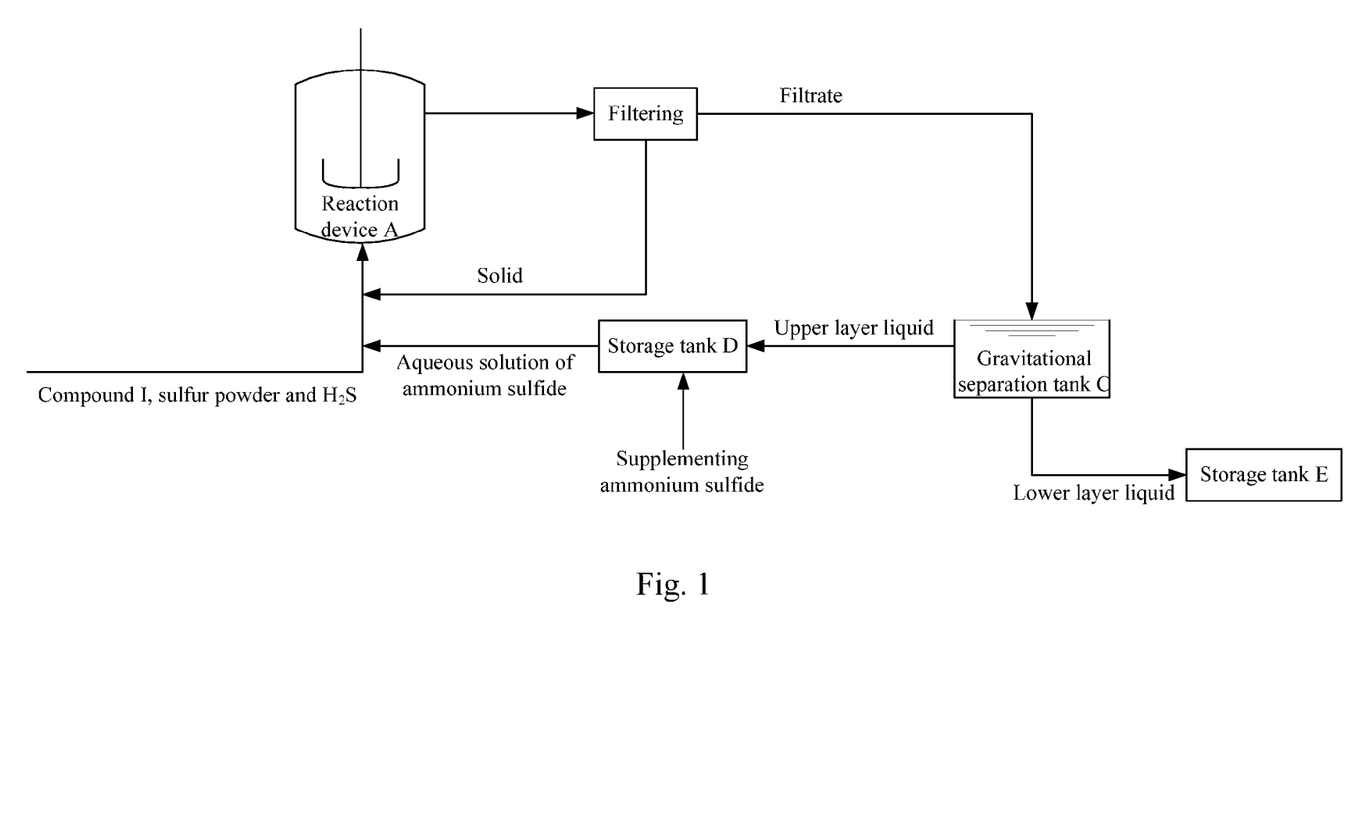
FIG. 1 is a process flow sheet of a preferred embodiment of a process for preparing a compound of formula II according to the present application.

As shown in FIG. 1, in one particularly preferred embodiment, the process for preparing a compound of formula II comprises: continuously adding a compound of formula I, sulfur, H₂S and an aqueous solution of ammonium sulfide from the storage tank D into the reaction device A; after filtering the reaction solution overflowing the upper part of the reaction device A, returning the solid to the reaction device A while the filtrate flows into the gravitational separation tank C; making the upper layer liquid in the gravitational separation tank C firstly flow into the storage tank D for an aqueous solution of ammonium sulfide (timing measurement of the content of ammonium sulfide, and supplementation when the content of ammonium sulfide is insufficient), and then adding the resultant product to the reaction device A while the lower layer liquid flows into the storage tank E for the liquid mixture of a compound of formula II and a compound of formula III.

In another aspect, the present application is directed to a process for refining a mixture comprising a compound of formula II and a compound of formula III, comprising continuously adding the mixture and an aqueous solution of sodium sulfite to a second reaction device to carry out the following reaction, In some embodiments, the reaction for refining a mixture comprising a compound of formula II and a compound of formula III is carried out in 2 to 6 continuous extraction columns or reaction towers.

In some embodiments, the reaction for refining a mixture comprising a compound of formula II and a compound of formula III is carried out in 2 to 10 reaction kettles.

In some preferred embodiments, several continuous extraction columns or reaction towers or reaction kettles for refining a mixture comprising a compound of formula II and a compound of formula III may be connected in series or in parallel or partly in parallel.

In some preferred embodiments, the process of refining a mixture comprising a compound of formula II and a compound of formula III comprises:
1) continuously adding the mixture and an aqueous solution of sodium sulfite to a first counter-current extraction column; and
2) continuously adding the organic layer obtained from step 1) and water to a second counter-current extraction column to obtain a compound of formula II.

In some embodiments, the concentration of an aqueous solution of sodium sulfite is about 1-25%.

In some embodiments, the mixture and the 1-25% aqueous solution of sodium sulfite are fed into continuous extraction columns or reaction towers or reaction kettles at a total rate of 1 g to 100 kg per minute.

In some preferred embodiments, the mass ratio of the mixture and sodium sulfite (dry basis) is about 1:0.1-1.0.

In some more preferred embodiments, the mass ratio of the mixture and sodium sulfite (dry basis) is about 1:0.36.

In some preferred embodiments, the product obtained from the reaction of the mixture with sodium sulfite and water are fed into extraction columns or reaction kettles at a total speed of 1 g to 100 kg per minute with a mass ratio of about 1:0.1 to 10.

In some preferred embodiments, the product obtained from the reaction of the mixture with sodium sulfite and water are fed into extraction columns or reaction kettles at a total speed of 1 g to 100 kg per minute with a mass ratio of about 1:1.

In some embodiments, the reaction for refining a mixture comprising a compound of formula II and a compound of formula III is carried out at about 50-70° C.

Figure 2:
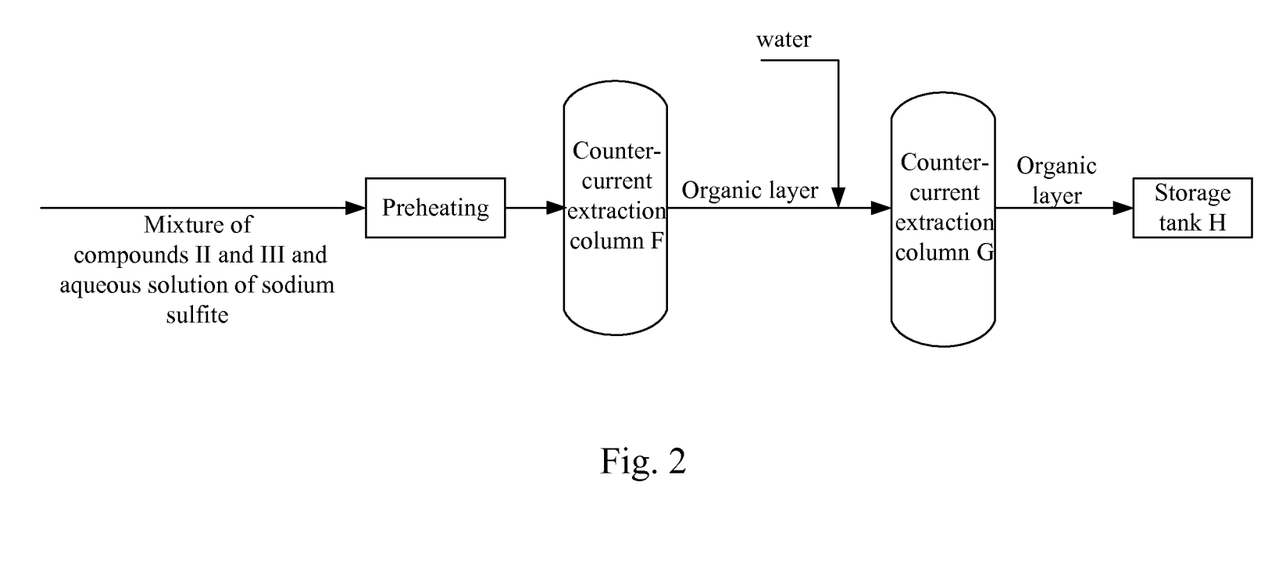
FIG. 2 is a process flow sheet of a preferred embodiment of a process for refining a mixture of a compound of formula II and a compound of formula III according to the present application.

As shown in FIG. 2, in one particularly preferred embodiment, a liquid mixture of a compound of formula II and a compound of formula III and an aqueous solution of sodium sulfite are preheated and added into the counter-current extraction column F, the resultant organic layer comprising a compound of formula II and water are then fed into the counter-current extraction column G, and the resultant refined organic layer flows into the storage tank H for a compound of formula II.

In still another aspect, the present application is directed to a process for preparing a compound of formula V, comprising continuously adding a compound of formula II and a primary amine of formula IV to a third reaction device to carry out the following reaction, wherein R represents $C_1$-$C_{18}$ alkyl or $C_3$-$C_{18}$ cycloalkyl.

In some embodiments, a process for preparing a compound of formula V comprises:
a) continuously adding a compound of formula II and a primary amine of formula IV to a third reaction device; and
b) subjecting the reaction products obtained from step a) to a solid-liquid separation to obtain a solid and a mother liquid, wherein the mother liquid is returned to the third reaction device.

In some embodiments, the content of the primary amine in the reacting mother liquid is about 5-50%.

The exemplary examples of a primary amine which can be used to prepare a compound of formula V include, but are not limited to, methylamine, ethylamine, n-propylamine, isopropylamine, n-butylamine, isobutylamine, t-butylamine, cyclohexylamine, n-octylamine, ethylene diamine, and the like.

In some preferred embodiments, the primary amine used to prepare a compound of formula V is methylamine.

In some preferred embodiments, a compound of formula II and the reacting mother liquid comprising 5-50% primary amine are fed into a third reaction device at a total speed of 1 g to 100 kg per minute.

In some preferred embodiments, the molar ratio of the compound of formula II and the reacting mother liquid comprising a primary amine (based on the primary amine) is about 1:0.2-2.2.

In some preferred embodiments, a third reaction device used in the process for preparing a compound of formula V comprises several reactors.

In some preferred embodiments, the reaction device comprises 1 to 10 reaction kettles.

In some more preferred embodiments, several reaction kettles may be connected in series or in parallel or partly in parallel.

In some preferred embodiments, the reaction device comprises 1 to 4 continuous reaction towers.

In some more preferred embodiments, several continuous reaction towers may be connected in series or in parallel or partly in parallel.

In some preferred embodiments, the process for preparing a compound of formula V further comprises:
c) washing the solid obtained from step b) with an alcohol.

In some embodiments, an alcohol used to wash the solid obtained from step b) is a lower alcohol.

In the process for preparing a compound of formula V, exemplary examples of an alcohol which can be used to wash the solid obtained from step b) include, but are not limited to, methanol, ethanol, n-propanol, isopropanol, n-butanol, isobutanol, s-butanol, t-butanol, n-pentanol, 2-pentanol, 3-pentanol, t-pentanol, isoamylol, hexanol, n-octanol, 2-octanol, n-nonanol, decanol, benzyl alcohol, tetrahydrofurfuryl alcohol, ethylene glycol, propane-1,2-diol, propane-1,3-diol, butane-1,3-diol, butane-2,3-diol, glycerol, penta-1,5-diol, furfuryl alcohol, 2-chloroethanol, 2-bromoethanol, and the like.

In some preferred embodiments, in the process for preparing a compound of formula V, the exemplary examples of an alcohol which can be used to wash the solid from b) include, but are not limited to, methanol, ethanol, n-propanol, isopropanol, n-butanol, isobutanol, s-butanol, t-butanol, and the like.

In some preferred embodiments, the solid obtained from step b) is washed with methanol.

In some embodiments, the reaction for preparing a compound of formula V is carried out at about 0-15° C.

In some embodiments, the reaction for preparing a compound of formula V is carried out for 10-96 hours.

Figure 3:
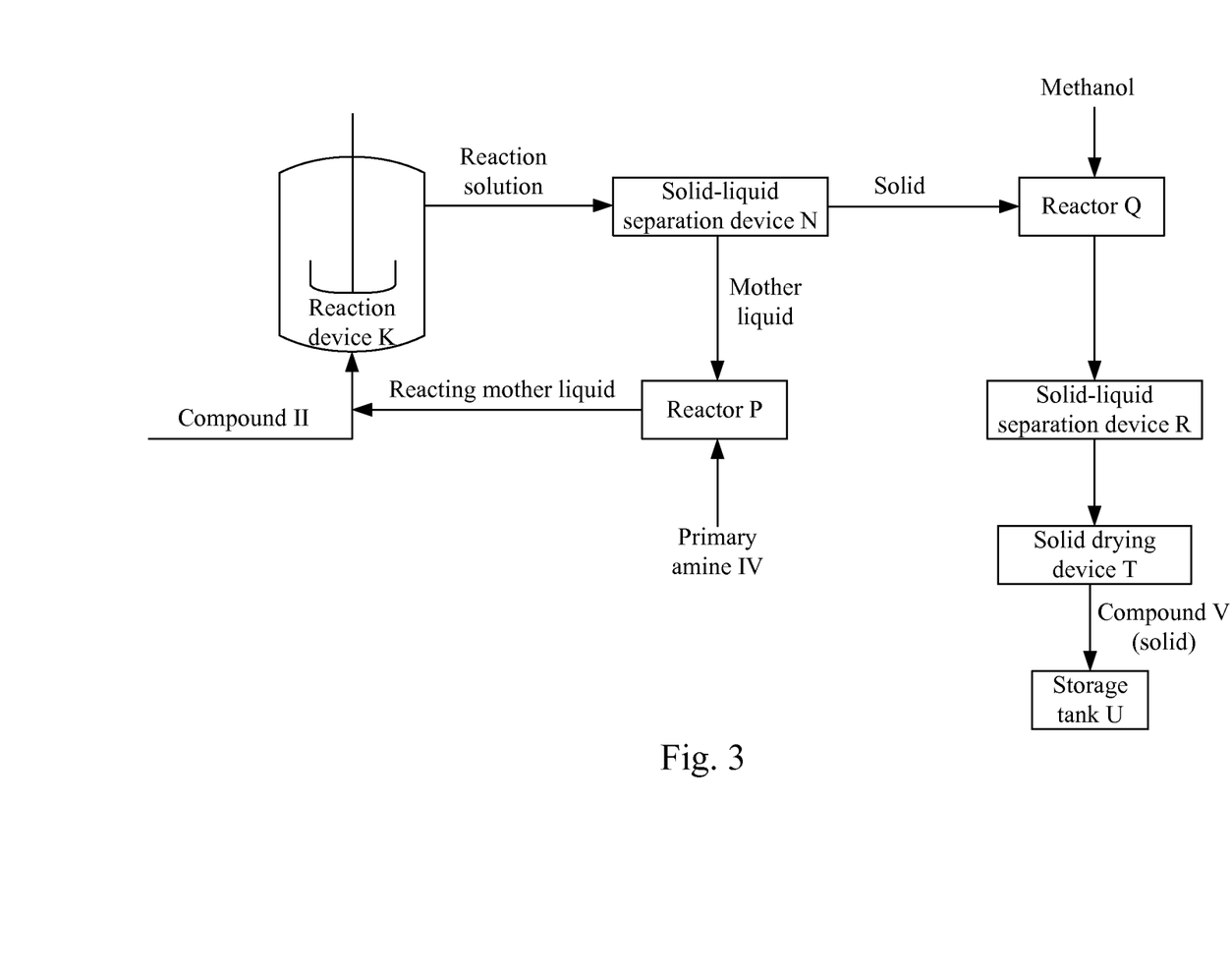
FIG. 3 is a process flow sheet of a preferred embodiment of a process for preparing a compound of formula V according to the present application.

As shown in FIG. 3, in one particularly preferred embodiment, the process comprises continuously adding a compound of formula II and the reacting mother liquid from the reactor P to the reaction device K, subjecting the reaction solution overflowing the upper part of the reaction device K and into the solid-liquid separation device N to a solid-liquid separation, and pumping the mother liquid after separation which enters the reactor P (the primary amine of formula IV flows into the reactor P at a certain speed) to the reaction device K; washing the solid which enters the reactor Q with methanol, and then carrying out a solid-liquid separation with the solid-liquid separation device R, followed by drying the obtained solid in the solid drying device T to obtain a compound of formula V, which enters the storage tank U.

In still another aspect, the present application is directed to a process for preparing a compound of formula VI, comprising continuously adding a compound of formula V and chlorine to a fourth reaction device to carry out the following reaction, wherein, IT =

R represents $C_1$-$C_{18}$ alkyl or $C_3$-$C_{18}$ cycloalkyl, and $R_1$ and $R_2$ independently represent H or chlorine.

In some embodiments, a process for preparing a compound of formula VI comprises:
A) continuously adding a compound of formula V and chlorine to a fourth reaction device; and
B) subjecting the reaction solution overflowing the fourth reaction device to a solid-liquid separation in order to obtain a solid and a mother liquid.

In some embodiments, the chloration reaction for preparing a compound of formula VI is carried out in the presence of an ester.

Exemplary examples of an ester include, but are not limited to, methyl formate, ethyl formate, propyl formate, isopropyl formate, butyl formate, isobutyl formate, isopentyl formate, benzyl formate, methyl acetate, ethyl acetate, ethyl acetoacetate, n-propyl acetate, isopropyl acetate, n-butyl acetate, isobutyl acetate, s-butyl acetate, pentyl acetate, isopentyl acetate, methyl amyl acetate, cyclohexyl acetate, benzyl acetate, methyl propionate, ethyl propionate, propyl propionate, n-butyl propionate, n-pentyl propionate, methyl n-butprate, ethyl n-butprate, n-butyl butyrate, methyl lactate, ethyl lactate, n-butyl lactate, pentyl lactate, diethyl oxalate, dibutyl oxalate, dipentyl oxalate, diethyl carbonate, tributyl carbonate, ethyl benzoate, isopropyl benzoate, ethyl salicylate, and the like.

In some preferred embodiments, in the process for preparing a compound of formula VI, exemplary examples of an ester that can be chlorated include, but are not limited to, ethyl acetate, n-propyl acetate, isopropyl acetate, n-butyl acetate, isobutyl acetate, s-butyl acetate, pentyl acetate, isopentyl acetate, methyl amyl acetate, cyclohexyl acetate, benzyl acetate, methyl propionate, ethyl propionate, propyl propionate, n-butyl propionate, n-pentyl propionate, methyl n-butprate, ethyl n-butprate, n-butyl butyrate, ethyl benzoate, isopropyl benzoate, and the like.

In some preferred embodiments, the chloration reaction for preparing a compound of formula VI is carried out in the presence of ethyl acetate.

In some preferred embodiments, a process for preparing a compound of formula VI comprises:
 A) continuously adding a compound of formula V, an ester and chlorine to a fourth reaction device;
 B) subjecting the reaction solution overflowing the upper part of the fourth reaction device to a solid-liquid separation to obtain a solid and a mother liquid, wherein the mother liquid is returned to the fourth reaction device; and
 C) washing the solid obtained from step B) with ethyl acetate to obtain a compound of formula VI.

In some preferred embodiments, the compound of formula V, chlorine and an ester are fed into the fourth reaction device at a total rate of 1 g to 100 kg per minute.

In some preferred embodiments, the mass ratio of the compound of formula V, chlorine and an ester is about 1:0.5-1.5:1-10.

In some embodiments, the fourth reaction device comprises 1 to 10 reaction kettles.

In some preferred embodiments, several reaction kettles may be connected in series or in parallel or partly in parallel.

In some embodiments, the fourth reaction device comprises 1 to 4 continuous reaction towers.

In some preferred embodiments, several continuous reaction towers may be connected in series or in parallel or partly in parallel.

In some embodiments, the reaction for preparing a compound of formula VI is carried out at 10-30° C.

Figure 4:
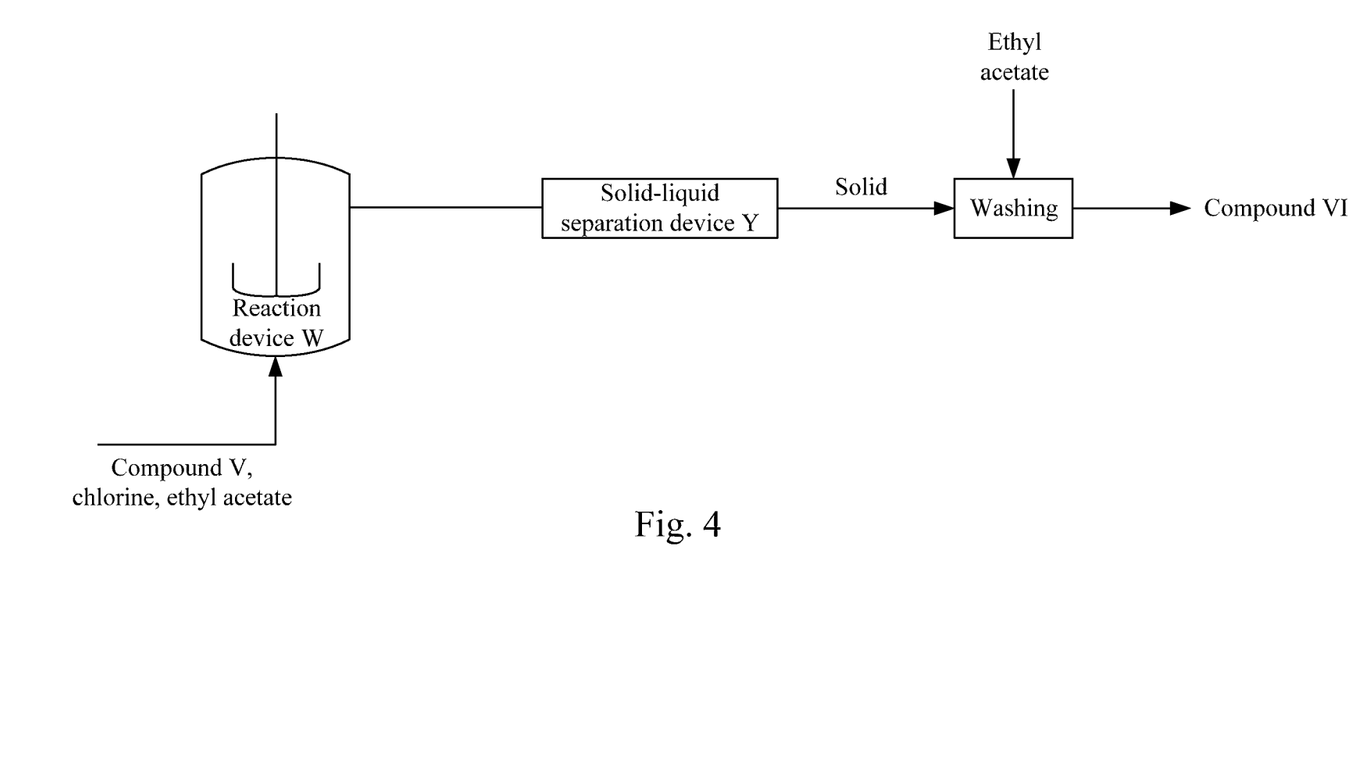
FIG. 4 is a process flow sheet of a preferred embodiment of a process for preparing a compound of formula VI according to the present application.

As shown in FIG. 4, in one particularly preferred embodiment, the process comprises continuously adding ethyl acetate, a compound of formula V and chlorine to the reaction device W, making the reaction solution overflowing the upper part of the reaction device W flow into the solid-liquid separation device Y, and washing the solid with ethyl acetate to obtain a compound of formula VI.

In yet another aspect, the present application is directed to a process for producing 3-isothiazolinone derivatives, comprising continuously carrying out the following four steps:
 1. continuously adding a compound of formula I, sulfur and $H_2S$ to a first reaction device to obtain a first reaction solution comprising a compound of formula II and a compound of formula III;
 2. continuously adding the first reaction solution and an aqueous solution of sodium sulfite to a second reaction device to obtain a second reaction solution comprising a compound of formula II;
 3. continuously adding the second reaction solution and a primary amine of formula IV to a third reaction device to obtain a compound of formula V; and
 4. continuously adding the compound of formula V and chlorine to a fourth reaction device to obtain a compound of formula VI.

In other aspects, the present application provides a process for producing 3-isothiazolinone derivatives, comprising two or more optional combinations of a process in each step aforementioned.

In some embodiments, the process for producing 3-isothiazolinone derivatives comprising continuously adding reaction solution comprising a compound of formula II and a primary amine of formula IV to a reaction device to obtain a compound of formula V, and then continuously adding the compound of formula V and chlorine to another reaction device to obtain a compound of formula VI.

In some embodiments, the process for producing 3-isothiazolinone derivatives comprises continuously adding a first reaction solution comprising a compound of formula II and a compound of formula III and an aqueous solution of sodium sulfite to a reaction device to obtain a second reaction solution comprising a compound of formula II; continuously adding the second reaction solution and a primary amine of formula IV to another reaction device to obtain a compound of formula V; and continuously adding the compound of formula V and chlorine to another reaction device to obtain a compound of formula VI.

Hereafter, detailed illustration will be carried out through the following examples referring to accompanying figures for better understanding of the various aspects and advantages of the present application. However, it will be appreciated that, the following examples is non-limiting and only for illustrating some embodiments of the present application.

EXAMPLES

Preparation of Ammonium Sulfide Base Solution

To a reaction kettle was firstly added water (820 kg), and then $NH_3$ (50 kg) and $H_2S$ (55 kg) were introduced under the temperature of 0-5° C. The resultant mixture was stirred for 30 minutes to obtain an ammonium sulfide base solution. The pH of the base solution was tested (target pH $\leqq 9.5$).

Example 1

Methyl acrylate (800 g), 10% ammonium sulfide base solution (520 g), sulfur (210 g) and liquid $H_2S$ (170 g) were continuously fed to the reaction kettle $A_1$ (50 L) from the bottom per minute. The resultant mixture was cooled to the temperature of 16-20° C. with stirring. The reaction solution overflowing the upper part (⅚ of the total height) of the reaction kettle $A_1$ flowed into the reaction kettle $A_2$ (50 L) from the bottom. The resultant mixture was cooled to the temperature of 16-20° C. with stirring. The reaction solution overflowing the upper part (⅚ of the total height) of the reaction kettle $A_2$ was filtered. The obtained solid was returned to the reaction kettle $A_1$ after being measured. The filtrate flowed into the gravitational separation tank C (100 L) from the middle of the tank C. The obtained upper layer liquid flowed into the storage tank D (50 L) for an aqueous solution of ammonium sulfide (timing measurement of the content of ammonium sulfide and supplementation when the content of ammonium sulfide is insufficient) and then was added to the reaction kettle $A_1$. The obtained lower layer liquid flowed into the storage tank E for a liquid mixture of a compound of formula II and a compound of formula III. The experiment was carried out for 12 hours to give 864 kg of a liquid mixture of a compound of formula II and a compound of formula III (compound of formula II: 68.5% and compound of formula III: 26.4% via chromatography analysis).

Example 2

Example 1 was repeated with a feeding speed of methyl acrylate (800 g), base solution comprising 9.5-10.5% ammonium sulfide (500 g), sulfur (220 g) and liquid $H_2S$ (190 g) per minute and a feeding period of 18 hours. 1309 kg of a liquid mixture of a compound of formula II and a formula of formula III was obtained from the storage tank E. Compound of formula II: 65.6% and compound of formula III: 28.7% via gas chromatography analysis.
Preparation of Sodium Sulfite Solution Into a reaction kettle was added water (2000 L). The water was heated to 40-45° C. with stirring. Into the reaction kettle was added solid sodium sulfite powder (225 kg). The resultant mixture was kept warm for about 30 minutes until the mixture was completely dissolved.

Example 3

A liquid mixture of a compound of formula II and a compound of formula III prepared in Example 1 and an aqueous solution of sodium sulfite (10%) were preheated to 65° C. The mixture and the aqueous solution of sodium sulfite were continuously added to the counter-current extraction column F having a diameter of 60 cm and a height of 2.5 m at a speed of 1200 g and 4270 g per minute, respectively. The obtained organic layer and water were further continuously added into another counter-current extraction column G having the same size to obtain a refined organic layer of the compound of formula II, which was collected in the storage tank H. The experiment was carried out for 10 hours to give 606 kg of the compound of formula II (96.5% via chromatography analysis).

Example 4

The speed of a liquid mixture of a compound of formula II and a compound of formula III and an aqueous solution of sodium sulfite (10%) were adjusted to 1500 g and 5340 g per minute, respectively. The operations of Example 3 were repeated. The period of continuously feeding the liquid mixture of the compound of formula II and the compound of formula III was also 10 hours to give 762 kg of the compound of formula II (compound of formula II: 93.4% and compound of formula III: 2.7% via gas chromatography analysis).
Preparation of Methylamine Solution Methanol (360 kg) was added to a glass lining kettle, stirred and cooled. The kettle was cooled to 0-5° C. Methylamine (180 kg) was introduced within a period of 3-4 hours. After the introduction, the mixture was stirred for 10 minutes while keeping warm. The resultant product was discharged and sealed for storage.

Example 5

The compound of formula II prepared according to Example 2 and a reacting mother liquid comprising methylamine (35%) were continuously added to the reaction kettle $K_1$ (50 L) from the bottom at a speed of 1 kg per minute and 3 kg per minute, respectively. The resultant product was cooled to 0-8° C. with stirring. The reaction solution overflowing the upper part (⅝ of the total height) of the reaction kettle $K_1$ flowed into the reaction kettle $K_2$ (50 L) from the bottom. The resultant mixture was cooled to the temperature of 0-8° C. with stirring. The reaction solution overflowing the upper part (⅝ of the total height) of the reaction kettle $K_2$ flowed into the kettles $K_3$ and $K_4$ in the same manner. The reaction solution overflowing the upper part (⅝ of the total height) of the reaction kettle $K_4$ alternately flowed into the centrifuges N1 and N2 having a diameter of 300 mm at a flowing speed of 4 kg/minute for a solid-liquid separation. The mother liquid entered the reaction kettle P (50 L) (in which liquid methylamine was continuously added to the kettle from the bottom at a speed of 0.26 kg/minute). The resultant product was subsequently pumped into the reaction kettle K1. The solid entered the reaction kettles Q1 and Q2 (50 L). The resultant mixture was washed with approximately equal mass of methanol and was subjected to a solid-liquid separation via the centrifuges R1 and R2 (300 mm), respectively. The solid was dried and entered the storage tank T. The experiment was carried out for 20 hours to give 498 kg of the compound of formula V (98.5% via chromatography analysis).

Example 6

The compound of formula II and a reacting mother liquid comprising n-octylamine (25%) were continuously added to the reaction kettle $K_1$ (50 L) from the bottom at a speed of 1 kg/minute and 8.7 kg/minute, respectively. The resultant mixture was cooled to the temperature of 30-35° C. with stirring. The reaction solution overflowing the upper part (⅝ of the total height) of the reaction kettle $K_1$ flowed into the reaction kettle $K_2$ (50 L) from the bottom. The resultant mixture was cooled to the temperature of 30-35° C. with stirring. The reaction solution overflowing the upper part (⅝ of the total height) of the reaction kettle $K_2$ flowed into the kettles $K_3$ and $K_4$ in the same manner. The reaction solution overflowing the upper part (⅝ of the total height) of the reaction kettle $K_4$ alternately flowed into the centrifuges N1 and N2 having a diameter of 300 mm at a flowing speed of 9.7 kg/minute for a solid-liquid separation. The mother liquid entered the reaction kettle P (50 L) (n-octylamine was continuously added into the kettle from the bottom at a speed of 1.16 kg/minute). The resultant mixture was subsequently pumped into the reaction kettle $K_1$. The solid entered the reaction kettles $Q_1$ and $Q_2$ (50 L), respectively. The resultant mixture was washed with approximately equal mass of methanol and subjected to a solid-liquid separation via the 300 mm centrifuges R1 and R2, respectively. The solid was dried and entered the storage tank T. The feeding of the compound of formula II and n-octylamine continued for 20 hours to give 902 kg of the compound of formula V in the storage tank T (98.6% via chromatography analysis). The reacting mother liquid continued to recycle for 50 hours and 945 kg of the compound of formula V was obtained from the storage tank T ($R=C_8H_{17}$, 98.4% via chromatography analysis).

Example 7

Ethyl acetate (2.2 kg), the compound of formula V (0.4 kg) prepared according to Example 3 and liquid chlorine (0.52 kg) were continuously added to the reaction kettle U (500 L) from the bottom per minute. The resultant mixture was cooled to the temperature of 18-22° C. with stirring. The reaction solution overflowing the upper part (⅝ of the total height) of the reaction kettle U sequentially flowed into the 300 mm centrifuges Y1, Y2 and Y3. The mother liquid flowed into the storage tank Z. The resultant mixture was then pumped into the reaction kettle U. The solid was washed with ethyl acetate and dried. The experiment was carried out for 8 hours to give 315 kg of the compound of formula VI (98.7% via chromatography analysis).

Example 8

Ethyl acetate (2.2 kg), the compound of formula V (R=$C_8H_{17}$) (0.4 kg) prepared according to Example 6 and liquid chlorine (0.19 kg) were continuously added to the reaction kettle W (500 L) from the bottom per minute. The resultant mixture was cooled to the temperature of 40-45° C. with stirring. The reaction solution overflowing the upper part (5/6 of the total height) of the reaction kettle W sequentially flowed into the 300 mm centrifuges Y1, Y2 and Y3. The solid was washed with ethyl acetate and dried. The experiment was carried out for 8 hours to give 215 kg of the compound of formula VI (R=$C_8H_{17}$, $R_1$=$R_2$=H, 98.2% via chromatography analysis).

It will be appreciated that, examples of the application only serve as non-limiting illustration for understanding of the present application. A person skilled in the art may make various equivalent replacements and modifications without deviating from the spirit and scope of the application, which still belong to the protection scope of the application.

The invention claimed is:

1. A process for producing 3-isothiazolinone derivatives, comprising continuously carrying out the following four steps:
(1) continuously adding a compound of formula I, sulfur and $H_2S$ to a first reaction device to obtain a first reaction solution comprising a compound of formula II and a compound of formula III by way of a first reaction:

wherein the first reaction is carried out in an aqueous solution of ammonium sulfide;
(2) continuously adding the first reaction solution and an aqueous solution of sodium sulfite to a second reaction device to obtain a second reaction solution comprising a compound of formula II by way of a second reaction:

wherein step (2) comprises i) continuously adding a mixture of a compound of formula II and a compound of formula III and an aqueous solution of sodium sulfite to a first counter-current extraction column; and
ii) continuously adding the organic phase obtained from step i) and water to a second counter-current extraction column to obtain the compound of formula II;
(3) continuously adding the second reaction solution and a primary amine of formula IV to a third reaction device to obtain a compound of formula V by way of a third reaction:

wherein R represents $C_1$-$C_{18}$ alkyl or $C_3$-$C_{18}$ cycloalkyl; and
(4) continuously adding the compound of formula V and chlorine to a fourth reaction device to obtain a compound of formula VI by way of a fourth reaction:

R represents $C_1$-$C_{18}$ alkyl or $C_3$-$C_{18}$ cycloalkyl, and $R_1$ and $R_2$ independently represent H or chlorine, and
the fourth reaction is carried out in the presence of an ester.

2. The process of claim 1, wherein the step (1) comprises:
i) continuously adding a compound of formula I, sulfur and $H_2S$ to a first reaction device to cause the first reaction solution to overflow from the first reaction device; and
ii) filtering the first reaction solution overflowing the first reaction device to obtain a solid and a two-phase filtrate, wherein the solid and water phase are returned to the first reaction device.

3. The process of claim 1, wherein the mass ratio of the compound of formula I, ammonium sulfide, sulfur and $H_2S$ in the step (1) is about 1:0.01-0.25:0.2-0.5:0.2-0.3.

4. The process of claim 1, wherein the reaction in the step (1) is carried out at about 15-25° C.

5. The process of claim 1, wherein the second reaction is carried out at about 50-70° C.

6. The process of claim 1, wherein the step (3) comprises:
i) continuously adding a compound of formula II and a primary amine of formula IV to the third reaction device; and
ii) subjecting the reaction products obtained from step i) to a solid-liquid separation, and returning the obtained mother liquid to the third reaction device.

7. The process of claim 1, wherein the molar ratio of the compound of formula II and a reacting mother liquid comprising a primary amine (based on the primary amine) in the step (3) is about 1:0.2-2.2.

8. The process of claim 1, wherein the third reaction is carried out at about 0-15° C.

9. The process of claim 1, wherein the primary amine in the step (3) is selected from the group consisting of methylamine, ethylamine, n-propylamine, isopropylamine, n-butylamine, isobutylamine, t-butylamine, cyclohexylamine, n-octylamine and ethylene diamine.

10. The process of claim 9, wherein the primary amine is selected from the group consisting of methylamine and n-octylamine.

11. The process of claim 6, further comprising iii) washing the solid obtained from step ii) with alcohols.

12. The process of claim 1, wherein the third reaction is carried out in methanol.

13. The process of claim 1, wherein the step (4) comprises:
   i) continuously adding a compound of formula V and chlorine to the fourth reaction device to cause the fourth reaction solution to overflow from the fourth reaction device; and
   ii) subjecting the fourth reaction solution overflowing the fourth reaction device to a solid-liquid separation in order to obtain a solid and a mother liquid.

14. The process of claim 1, wherein the mass ratio of the compound of formula V, chlorine and the ester in the step (4) is about 1:0.5-1.5:1-10.

15. The process of claim 1, wherein the fourth reaction is carried out at 10-50° C.

* * * * *